United States Patent [19]

Yanagida et al.

[11] Patent Number: 5,686,086
[45] Date of Patent: Nov. 11, 1997

[54] EXTERNAL SKIN TREATMENT COMPOSITION

[75] Inventors: Takeshi Yanagida; Sakamoto Okihiko, both of Yokohama, Japan

[73] Assignee: Shiseido Co., Ltd., Tokyo, Japan

[21] Appl. No.: 616,914

[22] Filed: Mar. 18, 1996

Related U.S. Application Data

[63] Continuation of Ser. No. 204,304, filed as PCT/JP93/00968, Jul. 13, 1993, abandoned.

[30] Foreign Application Priority Data

Jul. 13, 1992 [JP] Japan .................................. 4-227723
Jul. 13, 1992 [JP] Japan .................................. 4-227724
Jul. 13, 1992 [JP] Japan .................................. 4-227726

[51] Int. Cl.$^6$ ............................................. A61K 7/48
[52] U.S. Cl. ......................... 424/401; 424/64; 424/78.02; 514/725; 514/844; 514/845; 514/846; 514/847; 514/937
[58] Field of Search ............................ 424/401, 78.02, 424/64; 514/725, 844–847, 937

[56] References Cited

U.S. PATENT DOCUMENTS

| | | | |
|---|---|---|---|
| 4,678,663 | 7/1987 | Scott et al. ........................ | 424/62 |
| 4,743,442 | 5/1988 | Raaf et al. ........................ | 424/47 |
| 4,938,960 | 7/1990 | Ismail ............................... | 424/195.1 |
| 5,013,726 | 5/1991 | Ivy et al. .......................... | 514/159 |

FOREIGN PATENT DOCUMENTS

| | | |
|---|---|---|
| 158090 | 10/1985 | European Pat. Off. . |
| 255364 | 2/1988 | European Pat. Off. . |
| 273202 | 7/1988 | European Pat. Off. . |
| 0 512 814 | 11/1992 | European Pat. Off. . |
| 1 792 514 | 1/1970 | Germany . |
| 3327840 | 9/1984 | Germany . |
| 3431755 | 3/1985 | Germany . |
| 57-131716 | 8/1982 | Japan . |
| 58-140008 | 8/1983 | Japan . |
| 59-95210 | 6/1984 | Japan . |
| 62-419 | 1/1987 | Japan . |
| 63-10710 | 1/1988 | Japan . |
| 63-2926 | 1/1988 | Japan . |
| 63-135309 | 6/1988 | Japan . |
| 63-258807 | 10/1988 | Japan . |
| 64-40412 | 2/1989 | Japan . |
| 163031 | 3/1989 | Japan . |
| 1-186811 | 7/1989 | Japan . |
| 1186809 | 7/1989 | Japan . |
| 1186811 | 7/1989 | Japan . |
| 1-246208 | 10/1989 | Japan . |
| 2-142713 | 5/1990 | Japan . |
| 2-502546 | 8/1990 | Japan . |
| 8503434 | 8/1985 | WIPO . |
| 8606275 | 11/1986 | WIPO . |
| 88/04539 | 12/1988 | WIPO . |

*Primary Examiner*—Jyothsan Venkat
*Attorney, Agent, or Firm*—Foley & Lardner

[57] ABSTRACT

An external skin treatment composition comprising (i) vitamin A and (ii) at least one skin roughening improvement aid selected from the group consisting of (a) polyoxyalkylene modified organopolysiloxanes, (b) sugars, and (c) anti-inflammatory agents.

4 Claims, No Drawings

EXTERNAL SKIN TREATMENT COMPOSITION

This application is a continuation, of application Ser. No. 08/204,304, filed as PCT/JP93/00968 Jul. 13, 1993 now abandoned.

TECHNICAL FIELD

The present invention relates to an external skin treatment composition and, more specifically, it relates to an external skin treatment composition having a synergistically improved skin roughening improvement effect by incorporating thereinto vitamin A and a polyoxyalkylene modified organopolysiloxane, a sugar or an anti-inflammatory agent, with taking safety into consideration.

BACKGROUND ART

Various pharmaceutically effective components are formulated into external skin treatment compositions. Among these pharmaceutical effects, an effect, by which the changes in the skin due to aged skin or sunlight exposure etc. are prevented or improved, is one of such effects, and therefore, an external skin treatment compositions such as cosmetic compositions having such purposes have been desired.

Under such circumstances, various raw materials extracted from natural products, such as proteins, polysaccharides, extracted extracts, natural polymers etc. have been heretofore formulated in external skin treatment compositions due to their characteristics application effects.

Recently, Japanese Unexamined Patent Publication (Kokai) No. 64-500355 discloses a method for preventing or improving the changes or disabilities caused due to aged skins or sunlight exposure by formulating thereinto at least one component selected from vitamin A and the derivatives thereof.

However, the effects thereof are not sufficient and it has been strongly desired to develop a pharmaceutically effective agent having much more excellent effects.

DISCLOSURE OF THE INVENTION

Accordingly, the objects of the present invention are to obviate the above-mentioned problems in the prior art and to provide an external skin treatment composition having sufficient skin roughening improvement effects, i.e., prevention effects, improvement effects, etc. against the changes or disabilities due to aged skin or sunlight exposure.

In accordance with the present invention, there is provided an external skin treatment composition comprising (i) vitamin A and (ii) at least one skin roughening improvement aid selected from the group consisting of (a) polyoxyalkylene modified organopolysiloxanes, (b) sugars, and (c) anti-inflammatory agents.

BEST MODE FOR CARRYING OUT THE INVENTION

In order to achieve the above-mentioned objects, the present inventors have been extensibly studied to obtain a substance or substances capable of effecting sufficient skin roughening improvement effects, especially, among substances having excellent safety and, as a result, found that the above-mentioned problems can be solved by formulating, together with vitamin A, polyoxyalkylene modified organopolysiloxanes, sugars or anti-inflammatory agents.

The constitution of the present invention will now be explained in detail.

Vitamin A used in the present invention is also called retinol and is usually used in the treatment of infant or childhood diseases or nyctalopia (i.e., night blindness) or in the recovery agent after pregnancy in the pharmaceutical fields etc. Among these, all-trans products or 13-cis products can be preferably used, but the mixture thereof can also be used.

There are no limitations to the amounts of vitamin A formulated into the external skin treatment agent according to the present invention, but the preferable amount is 0.00001 to 5% by weight, more preferably 0.0001 to 0.5% by weight, in view of the effect of vitamin A to the skin.

The polyoxyalkylene modified organopolysiloxanes usable as a skin toughening improvement aid, in the present invention are the following compounds (A), (B), (C) and (D).

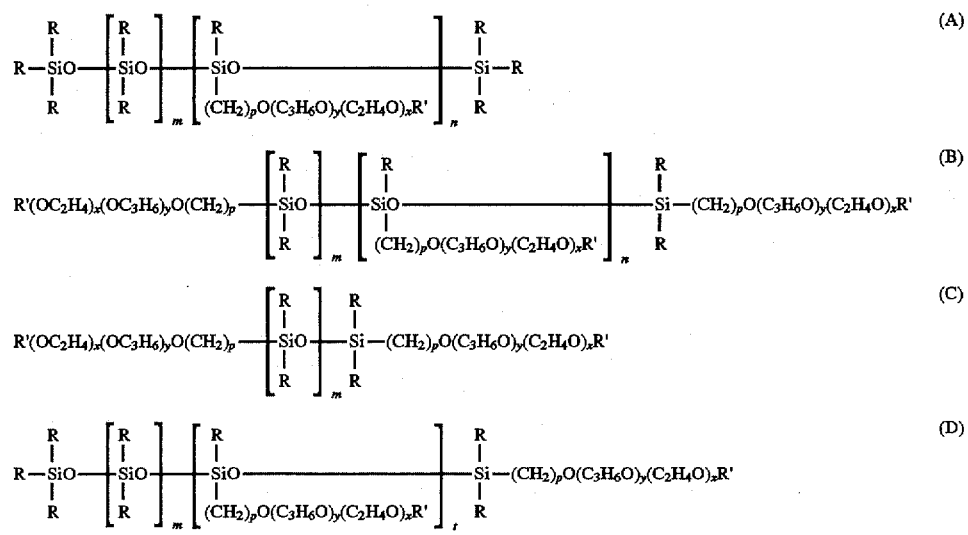

wherein R represents an alkyl group having 1 to 3 carbon atoms, or a phenyl group, R' represents hydrogen or an alkyl group having 1 to 12 carbon atoms, p is an integer of 1 to 5, m is an integer of 5 to 100, n and x are an integer of 1 to 50 and t and y are an integer of 0 to 50.

There are no specific limitations to the average molecular weight of the polyoxyalkylene modified organopolysiloxane usable in the present invention, but the preferable molecular weight is 3,000 or more, further preferably 5,000 to 10,000. Furthermore, the preferable polyoxyalkylene modified organopolysiloxanes are those having 2–80% by weight, more preferable, 11–50% by weight in view of the generation of the effects, of polyoxyalkylene group in the molecule thereof.

The amount of the polyoxyalkylene modified organopolysiloxane formulated is preferably 0.1 to 20% by weight, more preferably 0.2 to 10% by weight, in the total amount of the external skin treatment composition. When the amount is less than 0.1% by weight, there are fears that the skin irritation is not sufficiently lowered. Contrary to this, when the amount is more than 20% by weight, there are fears that the qualities necessary as the skin treatment composition cannot be held.

In the present invention, as the sugars usable as a skin roughening improvement aid, mention may be made of monosaccharides, oligosaccharides, sugar alcohols, etc.

As the monosaccharides, mention may be made of trioses such as D-glycerylaldehyde, dihydroxyaceton, etc., tetroses such as D-erythrose, D-erythrolose, D-threose, etc., pentoses such as L-arabinose, D-xylose, L-lyxose, D-arabinose, D-ribose, D-ribulose, D-xylulose, L-xylulose, etc., hexoses such as D-glucose, D-talose, D-psicose, D-galactose, D-fructose, L-galactose, L-sorbose, D-mannose, D-tagalose etc., heptoses such as aldoheptose, heptalose etc., octoses such as octose etc., deoxy sugars such as 2-deoxy-D-ribose, 6-deoxy-L-galactose, 6-deoxy-L-mannose, etc., amino sugars such as D-glucosamine, D-galactosamine, sialic acid, aminouronic acid, muramic acid, etc., uronic acids such as D-glucuronic acid, D-mannuronic acid, L-gluconic acid, D-galacturonic acid, L-iduronic acid etc.

As the oligo sugars, mention may be made of sucrose, gentianose, umbelliferose, lactose, planteose, α,α-trehalose, raffinose, umbilicin, stachyose, verbascoses.

Furthermore, as the sugar alcohols, mention may be made of sorbitol, maltitol, maltriose, mannitol, starch decomposed sugar, erythritol, xylitose, starch decomposing sugar reduced alcohols. Of these sugar alcohols, mannitol, erythritol and sugar alcohols of disaccharides or more.

There are no specific limitations to the amount of the sugars formulated, the preferable amount is at least 0.1% by weight, more preferably 0.5 to 50% by weight, based on the total amount of the external skin treatment agent. When the amount is less than 0.1% by weight, it is not preferable because it is difficult to obtain the synergistical skin roughening improvement effects according to the present invention.

Examples of anti-inflammatory agents usable as the skin roughening improvement aid according to the present invention are hydrocortisone, hydrocortisone acetate, prednisolone, methyl prednisolone, prednisolone acetate, prednisolone acetate propionate, dexamethasone, betamethasone, triamcinolone, dexamethasone acetate, betamethasone valerate, triamcinolone acetnide, aspirin, salicylic acid, acetaminophen, methyl salicylate, glycol salicylate, mefenamic acid, flufenamic acid, indometacin, diclofenac, ketoprofen, ibuprofen, flurbiprofen, fenbufen, lufexamac, piroxicam, oxyphenbutazone, mepirizole, ibuprofen piconol, clidanac, phenylbutazone, naproxen, glycyrrhetin, glycyrrhizin, glycyrrhetic acid and the salts and esters thereof, glycyrrhizic acid and the salts and esters thereof, azulene, camphor, thymol, allantoin, etc. Among these agents, one or more agents may be freely selected. Although the amount of the anti-inflammatory agents formulated in the present invention is not specifically limited, the preferable amount is 0.0001 to 5.0% by weight, more preferably 0.001 to 2% by weight, based upon the total amount of the external skin treatment composition. When the amount is less than 0.0001% by weight, there are fears that the reduction of the skin irritation, which is the effect of the present external skin treatment composition, cannot be achieved. Contrary to this, even when the anti-inflammatory agent is formulated in an amount of more than 5.0% by weight, further improvement is not expected.

In addition to the above-mentioned essential components, the external skin treatment composition according to the present invention may contain various components conventionally formulated into cosmetics, quasi-drugs, drugs such as aqueous components, humectants, thickeners, UV absorbers, antiseptics, antioxidants, flavours, colorants, medicines, crude drugs, in an amount such that the desired effects of the present invention are not impaired. It should be, of course, noted that these additives are used in such quantitative, qualitative conditions that the objects of the present invention are not impaired.

The external skin treatment composition according to the present invention can be in any form, for example, in the form of a solubilized type such as cosmetic lotions, an emulsified type such as Emulsions, creams, ointments, powder dispersion type, water-oil two layer type, water-oil-powder three layer type, etc.

EXAMPLES

The present invention will now be further illustrated by no means limited to, the following Examples, in which the amounts formulated are "% by weight".

Examples 1-1 to 1-5

Creams having the following compositions were prepared and the skin toughening improvement effects thereof were studied.

The polyoxyalkylene modified organopolysiloxanes listed in Table 1-1 were formulated.

|  | % |
|---|---|
| (1) Cetostearyl alcohol | 3.5 |
| (2) Squalane | 30.0 |
| (3) Beeswax | 3.0 |
| (4) Reduced lanolin | 5.0 |
| (5) Ethylparaben | 0.3 |
| (6) Polyoxyethylene (50 mol) oleyl alcohol ether | 2.0 |
| (7) Stearic monoglyceride | 2.0 |
| (8) Polyoxyalkylene modified organopolysiloxane (see Table 1-1) | 3.0 |
| (9) Perfume | 0.03 |
| (10) Vitamin A | 0.0001 |
| (11) Glycerol | 15.0 |
| (12) Purified water | Balance |

(Preparation Method)

(1), (2), (3), (4), (5), (6), (7), (8), (9) and (10) were heated and dissolved. The resultant solution was maintained at 75° C., followed by adding thereto, under stirring, (11) and (12) heated to 75° C. The mixture was stirred and emulsified in a homomixer, followed by cooling to obtain a cream.

Comparative Example 1-1

The same formulation except that the polyoxyalkylene modified organopolysiloxane was removed from the formulation of Example 1-1.

Comparative Example 1-2

The same formulation except that the vitamin A was removed from the formulation of Example 1-1.

TABLE 1-1

| No. | Polyoxyalkylene modified organosiloxane |
|---|---|
| Example 1-1 | General formula A<br>Polyxyethylene group 20 wt %, M.W. 6,000 |
| Example 1-2 | General formula A<br>Polyoxyethylene group 40 wt %, M.W. 20,000 |
| Example 1-3 | General formula B<br>Polyoxyethylene group 60 wt %, M.W. 10,000 |
| Example 1-4 | General formula C<br>Polyoxyethylene group 20 wt %<br>Polyoxypropylene group 10 wt %, M.W. 4,000 |
| Example 1-5 | General formula A<br>Polyoxyethylene group 15 wt %, M.W. 2,500 |

Skin Roughening Improvement Test Method

One hundred subjects having psoriasis-like and skin-roughening-like skin affections were divided into 5 groups as test panels and the creams of Examples 1-1 to 1-5 and Comparative Examples 1-1 to 1-2 were used by one group (20 members) each. That is, Examples 1-1 to 1-5 samples were applied to the left-side faces of the panel twice a day and Comparative Examples 1-1 and 1-2 were applied to the right-side faces of the panel for continuous 3 months. Thereafter, the degree of the overall improvements after the use was visually determined, when compared before the use.

The results are shown in Table 1-2.

Example 1-6: Cosmetic Lotion

| | % |
|---|---|
| (1) Vitamin A | 0.00001 |
| (2) Polyoxyalkylene modified organopolysiloxane*¹ | 0.1 |
| (3) Glycerol | 1.0 |
| (4) D-mannitol | 0.5 |
| (5) Purified water | Balance |
| (6) Ethanol | 7.0 |
| (7) Polyoxyethylene (50 mol) oleyl alcohol ether | 1.0 |
| (8) Methylparaben | 0.05 |
| (9) Oleyl alcohol | 1.0 |
| (10) Lactic acid | 0.01 |
| (11) Sodium lactate | 0.1 |
| (12) Perfume | 0.01 |

*¹: General formula B (Polyoxyethylene group 60 wt %, M. W. 10000)

(Preparation Method)

In the purified water, (3), (10) and (11) were dissolved. Separately, (1), (2), (7), (8) and (12) were dissolved in ethanol and this solution was added to the above purified water to be dissolved, followed by filtration. Thus, the cosmetic lotion was obtained. The cosmetic lotion of the present invention was excellent in the skin roughening improvement effects.

TABLE 1-2

Test Results of Practical Use (Degree of Overall Improvement)

| | Example | | | | | | | | | | Comparative Example | | | |
|---|---|---|---|---|---|---|---|---|---|---|---|---|---|---|
| | 1-1 | | 1-2 | | 1-3 | | 1-4 | | 1-5 | | 1-1 | | 1-2 | |
| Degree of overall improvement | Psoriasis | Skin roughening | Psoriasis | Skin roughening | Psoriasis | Skin roughening | Psoriasis | Skin roughening | Psoriasis | Skin roughening | Psoriasis | Skin roughening | Psoriasis | Skin roughening |
| Remarkable improvement | 7 | 6 | 6 | 6 | 6 | 7 | 6 | 6 | 5 | 5 | 0 | 0 | 0 | 0 |
| Some improvement | 2 | 2 | 3 | 2 | 1 | 2 | 2 | 2 | 3 | 3 | 4 | 4 | 1 | 1 |
| No change | 1 | 2 | 1 | 2 | 3 | 1 | 2 | 2 | 2 | 2 | 19 | 19 | 24 | 24 |
| Change for the worse | 0 | 0 | 0 | 0 | 0 | 0 | 0 | 0 | 0 | 0 | 2 | 2 | 0 | 0 |
| Total (No. of Person) | 10 | 10 | 10 | 10 | 10 | 10 | 10 | 10 | 10 | 10 | 25 | 25 | 25 | 25 |
| Degree of effectiveness % Those better than "some improvement" | 90 | 80 | 90 | 80 | 70 | 90 | 80 | 80 | 80 | 80 | 16 | 16 | 4 | 4 |

As is clear from the results shown in Table 1-2, the products of Examples 1-1 to 1-5 according to the present invention had synergistically excellent skin roughening improvement effects when compared with those of Comparative Examples 1-1 and 1-2.

Example 1-7: Pack

| | % |
|---|---|
| (1) Polyoxyalkylene modified organopolysiloxane*² | 3.0 |
| (2) Polyvinyl alcohol | 10.0 |
| (3) Propylene glycol | 7.0 |
| (4) Ethanol | 10.0 |
| (5) Vitamin A | 0.01 |

| | % |
|---|---|
| (6) Methylparaben | 0.05 |
| (7) POE (60 mol) hydrogenated castor oil | 0.2 |
| (8) Perfume | 0.05 |
| (9) Purified water | Balance |

*2: General formula A (Polyoxyethylene group 40 wt %, M.W. 8000)

(Preparation Method)

(1), (3), (6) and (7) were added to (7) and dissolved under stirring. Then, (2) was added thereto and stirred under heating, followed by adding thereto (4) containing (9) dissolved therein. The mixture was dissolved while stirring to obtain the pack.

The present pack had excellent skin roughening improvement effects.

Example 1-8: Compact Face Powder

| | % |
|---|---|
| (1) Vitamin A | 0.0005 |
| (2) Talc | 85.4 |
| (3) Stearic acid | 2.5 |
| (4) Squalane | 3.5 |
| (5) Sorbitan sesquioleic ester | 1.8 |
| (6) Triethanolamine | 1.2 |
| (7) Polyoxyalkylene modified organopolysiloxane*3 | 10.0 |
| (8) Glycyrrhetic stearyl | 0.1 |
| (9) Pigment | q.s. |
| (10) Perfume | q.s. |

*3: General formula B (polyoxyethylene group 60 wt %, M.W. 4000)

(Preparation Method)

The talc and the pigment were sufficiently mixed by a kneeder (Powder portion). The triethanolamine was added to 50% corresponding amount of the purified water and the mixture was maintained at 70° C. (Aqueous phase). The components of the present invention other than the perfume were mixed and dissolved under heating at 70° C. (Oil phase). The oil phase was added to the aqueous phase, followed by uniformly emulsified by a homomixer and the resultant emulsified mixture was added to the powder portion, followed by kneading the same by a kneeder, followed by evaporating the water and by treating the same by a grinder. Furthermore, the perfume was uniformly sprayed and the resultant product was compression molded.

The resultant compact face powder was excellent in the improvement effects to the skin.

Example 1-9: Lipstick

| | % |
|---|---|
| (1) Vitamin A | 0.00001 |
| (2) Microcrystalline wax | 3.0 |
| (3) Beeswax | 3.0 |
| (4) Ceresin wax | 5.0 |
| (5) Liquid paraffin | 19.0 |
| (6) Squalane | 20.0 |
| (7) Carnauba wax | 3.0 |
| (8) Candelilla wax | 3.0 |

| | % |
|---|---|
| (9) Polyoxyalkylene modified organopolysiloxane*4 | 1.0 |
| (10) Mixed colorant | 7.0 |
| (11) Dibutyl hydroxytoluene | 0.05 |
| (12) Perfume | q.s. |
| (13) Lanolin | Balance |

*4: General formula A (Polyoxyethylene group 60 wt %, M.W. 25000)

(Preparation Method)

The lipstick was obtained in a conventional way. The present lipstick exhibited remarkable prevention of the generation of roughening on the lips.

Example 1-10: Emulsion

| | % |
|---|---|
| (1) Vitamin A | 1.0 |
| (2) Polyoxyalkylene modified organopolysiloxane*5 | 1.0 |
| (3) Ethanol | 2.0 |
| (4) Glycerol | 10.0 |
| (5) Sorbitol 70% solu. | 3.0 |
| (6) Propylene glycol | 3.0 |
| (7) Carboxyvinyl polymer | 0.3 |
| (8) KOH | 0.1 |
| (9) Methylparaben | 0.1 |
| (10) Cetanol | 2.5 |
| (11) Vaseline | 2.0 |
| (12) Squalane | 10.0 |
| (13) Isopropyl myristate | 5.0 |
| (14) Glyceryl monostearate | 2.0 |
| (15) POE (25 mol) cetyl ether | 2.0 |
| (16) Purified water | Balance |

*5: General formula C (Polyoxyethylene group 15 wt %, Polyoxypropylene group 10 wt %, M.W. 5000)

(Preparation Method)

The present emulsion was obtained in a conventional way. The present emulsion exhibited excellent skin improvement effects.

Example 1-11: Emulsion

| | % |
|---|---|
| (1) Vitamin A | 0.3 |
| (2) Polyoxyalkylene modified organopolysiloxane*6 | 0.2 |
| (3) Ethanol | 5.0 |
| (4) Glycerol | 5.0 |
| (5) Sorbitol | 2.0 |
| (6) Propylene glycol | 5.0 |
| (7) Carboxyvinyl polymer | 0.2 |
| (8) KOH | 0.06 |
| (9) Methyl paraben | 0.2 |
| (10) POE (60 mol) hydrogenated castor oil | 1.0 |
| (11) Squalane | 3.0 |
| (12) Isopropyl myristate | 3.0 |
| (13) Indomethacin | 0.05 |
| (14) Purified water | Balance |

*6 General formula D (Polyoxyethylene group 40 wt %, M.W. 7000)

(Preparation Method)

The present emulsion was obtained in a conventional way. The present emulsion exhibited excellent skin improvement effects.

Example 1-12: Night Cream

|   | % |
|---|---|
| (1) Squalane | 20.0 |
| (2) Liquid paraffin | 10.0 |
| (3) Isopropyl myristate | 6.0 |
| (4) Butyl paraben | 0.2 |
| (5) Polyoxyalkylene modified organopolysiloxane*[7] | 3.0 |
| (6) Diglycerol diisostearate | 1.0 |
| (7) Vaseline | 4.0 |
| (8) Solid paraffin | 2.0 |
| (9) Vitamin A | 0.3 |
| (10) Propylene glycol | 4.0 |
| (11) Glycerol | 10.0 |
| (12) Magnesium sulfate | 0.3 |
| (13) Purified water | Balance |

*[7]: General formula A (Polyoxyethylene group 20 wt %, M.W. 6000)

(Preparation Method)

The present night cream was obtained in a conventional way. The present night cream exhibited excellent skin improvement effects.

Example 2-1 to 2-5

A cream having the following composition was prepared and the skin roughening improvement effects thereof were studied. The vitamin A and the sugars used are shown in Table 2-1 below.

|   | % |
|---|---|
| (1) Cetostearyl alcohol | 3.5 |
| (2) Squalane | 30.0 |
| (3) Beeswax | 3.0 |
| (4) Reduced lanolin | 5.0 |
| (5) Ethyl paraben | 0.3 |
| (6) Polyoxyethylene (50 mol) oleyl alcohol ether | 2.0 |
| (7) Stearic monoglyceride | 2.0 |
| (8) Sugar (see Table 2-1) | 0.5 |
| (9) Perfume | 0.03 |
| (10) Vitamin A (see Table 2-1) | 0.0001 |
| (11) Glycerol | 15.0 |
| (12) Purified water | Balance |

(Preparation Method)

(1), (2), (3), (4), (5), (6), (7), (8), (9) and (10) were heated and dissolved. The resultant solution was maintained at 75° C., followed by adding thereto, under stirring, (11) and (12) heated to 75° C. The mixture was stirred and emulsified in a homomixer, followed by cooling to obtain a cream.

Comparative Example 2-1

The same formulation except that the sugar was removed from the formulation of the above Example.

Comparative Example 2-2

The same formulation except that the vitamin A was removed from the formulation of the above Example.

TABLE 2-1

|   | Vitamin A | Sugars |
|---|---|---|
| Example 2-1 | all-trans | Sucrose |
| Example 2-2 | 13-cis | Maltitol |
| Example 2-3 | all-trans | D-mannitol |
| Example 2-4 | 13-cis | Sorbitol |
| Example 2-5 | all-trans | Fructose |
| Comp. Ex. 2-1 | 13-cis | None |
| Comp. Ex. 2-2 | None | Sorbitol |

Skin Roughening Improvement Test Method

One hundred subjects having psoriasis-like and skin-roughening-like skin affections were divided into 5 groups as test panels and the creams of Examples 2-1 to 2-5 and Comparative Examples 2-1 to 2-2 were used by one group (20 members) each. That is, Examples 2-1 to 2-5 samples were applied to the left-side faces of the panel twice a day and Comparative Examples 2-1 and 2-2 were applied to the right-side faces of the panel for continuous 3 months. Thereafter, the degree of the overall improvements after the use was visually determined, when compared before the use.

The results are shown in Table 2-2.

TABLE 2-2

Test Results of Practical Use (Degree of Overall Improvement)

| | Example | | | | | | | | | | Comparative Example | | | |
|---|---|---|---|---|---|---|---|---|---|---|---|---|---|---|
| | 2-1 | | 2-2 | | 2-3 | | 2-4 | | 2-5 | | 2-1 | | 2-2 | |
| Degree of overall improvement | Psoriasis | Skin roughening | Psoriasis | Skin roughening | Psoriasis | Skin roughening | Psoriasis | Skin roughening | Psoriasis | Skin roughening | Psoriasis | Skin roughening | Psoriasis | Skin roughening |
| Remarkable improvement | 7 | 6 | 6 | 6 | 6 | 7 | 6 | 6 | 5 | 5 | 0 | 0 | 0 | 0 |
| Some improvement | 2 | 2 | 3 | 2 | 1 | 2 | 2 | 2 | 3 | 3 | 4 | 4 | 5 | 5 |
| No change | 1 | 2 | 1 | 2 | 3 | 1 | 2 | 2 | 2 | 2 | 19 | 19 | 20 | 20 |
| Change for the worse | 0 | 0 | 0 | 0 | 0 | 0 | 0 | 0 | 0 | 0 | 2 | 2 | 0 | 0 |
| Total (No. of Person) | 10 | 10 | 10 | 10 | 10 | 10 | 10 | 10 | 10 | 10 | 25 | 25 | 25 | 5 |
| Degree of | | | | | | | | | | | | | | |

TABLE 2-2-continued

Test Results of Practical Use (Degree of Overall Improvement)

| | Example | | | | | | | | | | Comparative Example | | | |
| --- | --- | --- | --- | --- | --- | --- | --- | --- | --- | --- | --- | --- | --- | --- |
| | 2-1 | | 2-2 | | 2-3 | | 2-4 | | 2-5 | | 2-1 | | 2-2 | |
| Degree of overall improvement | Psoriasis | Skin roughening | Psoriasis | Skin roughening | Psoriasis | Skin roughening | Psoriasis | Skin roughening | Psoriasis | Skin roughening | Psoriasis | Skin roughening | Psoriasis | Skin roughening |
| effectiveness % Those better than "some improvement" | 90 | 80 | 90 | 80 | 70 | 90 | 80 | 80 | 80 | 80 | 16 | 16 | 20 | 20 |

As is clear from the results shown in Table 2-2, the products of Examples 2-1 to 2-5 according to the present invention had synergistically excellent skin roughening improvement effects when compared with those of Comparative Examples 2-1 and 2-2.

Example 2-6: Cosmetic Lotion

| | % |
| --- | --- |
| (1) Vitamin A | 0.1 |
| (2) D-xylose | 0.1 |
| (3) Glycerol | 1.0 |
| (4) Purified water | Balance |
| (5) Ethanol | 7.0 |
| (6) Polyoxyethylene (20 mol) oleyl alcohol ether | 0.5 |
| (7) Methyl paraben | 0.05 |
| (8) Citric acid | 0.01 |
| (9) Sodium citrate | 0.1 |
| (10) Camphor | 0.01 |
| (11) Perfume | 0.01 |

(Preparation Method)

In the purified water, (2), (3), (8) and (9) were dissolved. Separately, (1), (6), (7) and (11) were dissolved in ethanol and this solution was added to the above purified water to be dissolved, followed by filtration. Thus, the cosmetic lotion was obtained. The cosmetic lotion of the present invention was excellent in the skin roughening improvement effects.

Example 2-7: Pack

| | % |
| --- | --- |
| (1) D-mannose | 1.0 |
| (2) Polyvinyl alcohol | 10.0 |
| (3) Propylene glycol | 7.0 |
| (4) Ethanol | 10.0 |
| (5) Vitamin A | 0.01 |
| (6) Methyl paraben | 0.05 |
| (7) POE (60 mol) hydrogenated castor oil | 0.2 |
| (8) Perfume | 0.05 |
| (9) Purified water | Balance |

(Preparation Method)

In (9), (1), (3) and (6) were added, followed by stirring the mixture to thereby be dissolved. Then, (2) and (7) were added thereto, followed by heating while stirring to dissolve (9) therein. Thereafter, (4) was added, followed by stirring to be dissolved. Thus, the pack was obtained.

The present pack had a synergistically excellent skin roughening improvement effects.

Example 2-8: Compact Face Powder

| | % |
| --- | --- |
| (1) Vitamin A | 0.0005 |
| (2) Talc | 85.4 |
| (3) Stearic acid | 2.5 |
| (4) Squalane | 3.5 |
| (5) Sorbitan sesquioleic ester | 1.8 |
| (6) Triethanolamine | 1.2 |
| (7) D-glucosamine | 2.5 |
| (8) Pigment | q.s. |
| (9) Perfume | q.s. |

(Preparation Method)

The talc and the pigment were sufficiently mixed by a kneeder (Powder portion). The triethanolamine was added to 50% corresponding amount of the purified water and the mixture was maintained at 70° C. (Aqueous phase). The components of the present invention other than the perfume were mixed and dissolved under heating at 70° C. (Oil phase). The oil phase was added to the aqueous phase, followed by uniformly emulsified by a homomixer and the resultant emulsified mixture was added to the powder portion, followed by kneading the same by a kneeder, followed by evaporating the water and by treating the same by a grinder. Furthermore, the perfume was uniformly sprayed and the resultant product was compression molded.

The resultant compact face powder was excellent in the improvement effects to the skin.

Example 2-9: Lipstick

| | % |
| --- | --- |
| (1) Vitamin A | 0.00001 |
| (2) Microcrystalline wax | 3.0 |
| (3) Beeswax | 3.0 |
| (4) Ceresine wax | 5.0 |
| (5) Liquid paraffin | 19.0 |
| (6) Squalane | 20.0 |
| (7) Carnauba wax | 3.0 |
| (8) Candellira wax | 3.0 |
| (9) D-mannitol | 1.0 |
| (10) Mixed colorant | 7.0 |
| (11) Dibutyl hydroxytoluene | 0.05 |
| (12) Perfume | q.s. |
| (13) Lanolin | Balance |

(Preparation Method)

The lipstick was obtained in a conventional way. The present lipstick exhibited excellent skin improvement effects.

Example 2-10: Beauty Powder

|  | % |
|---|---|
| (1) D-mannitol | 50.0 |
| (2) D-sorbitol | 45.0 |
| (3) Vitamin A | 0.1 |
| (4) Talc | 4.9 |

(Preparation Method)

The present beauty powder was obtained in a conventional way. The present beauty powder exhibited excellent skin improvement effects.

Example 2-11: Emulsion

|  | % |
|---|---|
| (1) Vitamin A | 1.0 |
| (2) D-erithorlose | 2.5 |
| (3) Ethanol | 2.0 |
| (4) Glycerol | 10.0 |
| (5) Propylene glycol | 3.0 |
| (6) Carboxyvinyl polymer | 0.3 |
| (7) KOH | 0.1 |
| (8) Methyl paraben | 0.1 |
| (9) Cetanol | 2.5 |
| (10) Vaseline | 2.0 |
| (11) Squalane | 10.0 |
| (12) Isopropyl myristate | 5.0 |
| (13) Ibuprofen piconol | 0.01 |
| (14) Glyceryl monostearate | 2.0 |
| (15) POE(25 mol) cetyl ether | 2.0 |
| (16) Purified water | Balance |

(Preparation Method)

The present emulsion was obtained in a conventional way. The present emulsion exhibited excellent skin improvement effects.

Example 2-12: Emulsion

|  | % |
|---|---|
| (1) Vitamin A | 0.3 |
| (2) L-arabinose | 2.5 |
| (3) Ethanol | 5.0 |
| (4) Glycerol | 5.0 |
| (5) Propylene glycol | 5.0 |
| (6) Carboxyvinyl polymer | 0.2 |
| (7) KOH | 0.06 |
| (8) Methyl paraben | 0.2 |
| (9) POE(60 mol) hydrogenated castor oil | 1.0 |
| (10) Squalane | 3.0 |
| (11) Isopropyl myristate | 3.0 |
| (12) Monoammonium glycyrrhizinate | 0.05 |
| (13) Purified water | Balance |

(Preparation Method)

The present emulsion was obtained in a conventional way. The present emulsion exhibited synergistically excellent skin improvement effects.

Example 2-13: Night Cream

|  | % |
|---|---|
| (1) Squalane | 18.0 |
| (2) Liquid paraffin | 12.0 |
| (3) Isopropyl myristate | 7.0 |
| (4) Propyl paraben | 0.2 |
| (5) Diglycerine dioleate | 2.0 |
| (6) POE(5 mol) hydrogenated castor oil | 2.0 |
| (7) Vaseline | 6.0 |
| (8) Vitamin A | 0.5 |
| (9) Erithritol | 10.0 |
| (10) Sucrose | 5.0 |
| (11) Purified water | Balance |

(Preparation Method)

The present night cream was obtained in a conventional way. The present night cream exhibited synergistically excellent skin improvement effects.

Examples 3-1 to 3-5

Creams having the following compositions were prepared and the skin roughening improvement effects thereof were studied. The anti-inflammatory agents formulated are listed in Table 3-1.

|  | % |
|---|---|
| (1) Cetostearyl alcohol | 3.5 |
| (2) Squalane | 30.0 |
| (3) Beeswax | 3.0 |
| (4) Reduced lanolin | 5.0 |
| (5) Ethyl paraben | 0.3 |
| (6) Polyoxyethylene (50 mol) oleyl alcohol ether | 2.0 |
| (7) Stearic monoglyceride | 2.0 |
| (8) Anti-inflammatory (see Table 3-1) | 0.1 |
| (9) Perfume | 0.03 |
| (10) Vitamin A | 0.00001 |
| (11) Glycerol | 15.0 |
| (12) Purified water | Balance |

(Preparation Method)

(1), (2), (3), (4), (5), (6), (7), (8), (9) and (10) were heated and dissolved. The resultant solution was maintained at 75° C., followed by adding thereto, under stirring, (11) and (12) heated to 75° C. The mixture was stirred and emulsified in a homomixer, followed by cooling to obtain a cream.

Comparative Example 3-1

The same formulation except that the anti-inflammatory agents was removed from the formulation of Example 3-1.

Comparative Example 3-2

The same formulation except that the vitamin A was removed from the formulation of Example 3-1.

TABLE 3-1

|  | Drugs formulated |
|---|---|
| Example 3-1 | Glycyrrhizic ammonium |
| Example 3-2 | Allantoin |

TABLE 3-1-continued

| | Drugs formulated |
|---|---|
| Example 3-3 | Glycyrrhetic stearyl |
| Example 3-4 | Hydrocortisone |
| Example 3-5 | Acetaminophen |

Skin Roughening Improvement Test Method

One hundred subjects having psoriasis-like and skin-roughening-like skin affections were divided into 5 groups as test panels and the creams of Examples 3-1 to 3-5 and Comparative Examples 3-1 to 3-2 were used by one group (20 members) each. That is, Examples 3-1 to 3-5 samples were applied to the left-side faces of the panel twice a day and Comparative Examples 3-1 and 3-2 were applied to the right-side faces of the panel for continuous 3 months. Thereafter, the degree of the overall improvements after the use was visually determined, when compared before the use.

The results are shown in Table 3-2.

| | | %  |
|---|---|---|
| (11) | Sodium lactate | 0.1 |
| (12) | Perfume | 0.01 |

(Preparation Method)

In the purified water, (3), (4), (10) and (11) were dissolved. Separately, (1), (2), (7), (8) and (12) were dissolved in ethanol and this solution was added to the above purified water to be dissolved, followed by filtration. Thus, the cosmetic lotion was obtained. The cosmetic lotion of the present invention was excellent in the skin roughening improvement effects.

TABLE 3-2

Test Results of Practical Use (Degree of Overall Improvement)

| | Example | | | | | | | | | | Comparative Example | | | |
|---|---|---|---|---|---|---|---|---|---|---|---|---|---|---|
| | 3-1 | | 3-2 | | 3-3 | | 3-4 | | 3-5 | | 3-1 | | 3-2 | |
| Degree of overall improvement | Psoriasis | Skin roughening | Psoriasis | Skin roughening | Psoriasis | Skin roughening | Psoriasis | Skin roughening | Psoriasis | Skin roughening | Psoriasis | Skin roughening | Psoriasis | Skin roughening |
| Remarkable improvement | 7 | 6 | 6 | 6 | 6 | 7 | 6 | 6 | 5 | 5 | 0 | 0 | 0 | 0 |
| Some improvement | 2 | 2 | 3 | 2 | 1 | 2 | 2 | 2 | 3 | 3 | 4 | 4 | 3 | 3 |
| No change | 1 | 2 | 1 | 2 | 3 | 1 | 2 | 2 | 2 | 2 | 19 | 19 | 22 | 22 |
| Change for the worse | 0 | 0 | 0 | 0 | 0 | 0 | 0 | 0 | 0 | 0 | 2 | 2 | 0 | 0 |
| Total (No. of Person) | 10 | 10 | 10 | 10 | 10 | 10 | 10 | 10 | 10 | 10 | 25 | 25 | 25 | 25 |
| Degree of effectiveness % Those better than "some improvement" | 90 | 80 | 90 | 80 | 70 | 90 | 80 | 80 | 80 | 80 | 16 | 16 | 12 | 12 |

As is clear from the results shown in Table 3-2, the products of the present invention of Examples 3-1 to 3-5 had the synergistically excellent skin roughening improvement effects, when compared with the products of Comparative Examples 3-1 and 3-2.

Example 3-6: Cosmetic Lotion

| | | % |
|---|---|---|
| (1) | Vitamin A | 0.00001 |
| (2) | Bethamethasone | 0.01 |
| (3) | Glycerol | 1.0 |
| (4) | Maltitol | 0.3 |
| (5) | Purified water | Balance |
| (6) | Ethanol | 7.0 |
| (7) | Polyoxyethylene (50 mol) oleyl alcohol ether | 1.0 |
| (8) | Methyl paraben | 0.05 |
| (9) | Oleyl alcohol | 1.0 |
| (10) | Lactic acid | 0.01 |

Example 3-7: Pack

| | | % |
|---|---|---|
| (1) | Dexamethasone acetate | 0.5 |
| (2) | Polyvinyl alcohol | 10.0 |
| (3) | Propylene glycol | 7.0 |
| (4) | Ethanol | 10.0 |
| (5) | Vitamin A | 0.01 |
| (6) | Methyl paraben | 0.05 |
| (7) | POE(60 mol) hydrogenated castor oil | 0.2 |
| (8) | Perfume | 0.05 |
| (9) | Purified water | Balance |

(Preparation Method)

In (9), (1), (3), (6) and (7) were added, followed by stirring, whereby the mixture was dissolved. Then, (2) was added thereto and the mixture was stirred under heating.

Then, (4) containing (9) dissolved therein was added and stirred, whereby the mixture was dissolved to obtain the pack.

The present pack exhibited the excellent skin toughening improvement effects.

Example 3-8: Compact Face Powder

|  | % |
|---|---|
| (1) Vitamin A | 0.0005 |
| (2) Talc | 85.4 |
| (3) Stearic acid | 2.5 |
| (4) Squalane | 3.5 |
| (5) Sorbitan sesquioleic ester | 1.8 |
| (6) Triethanolamine | 1.2 |
| (7) Diclofenac | 0.01 |
| (8) Pigment | q.s. |
| (9) Perfume | q.s. |

(Preparation Method)

The talc and the pigment were sufficiently mixed by a kneeder (Powder portion). The triethanolamine was added to 50% corresponding amount of the purified water and the mixture was maintained at 70° C. (Aqueous phase). The components of the present invention other than the perfume were mixed and dissolved under heating at 70° C. (Oil phase). The oil phase was added to the aqueous phase, followed by uniformly emulsified by a homomixer and the resultant emulsified mixture was added to the powder portion, followed by kneading the same by a kneeder, followed by evaporating the water and by treating the same by a grinder. Furthermore, the perfume was uniformly sprayed and the resultant product was compression molded.

The resultant compact face powder was excellent in the improvement effects to the skin.

The present compact face powder exhibited excellent skin improvement effects.

Example 3-9: Lipstick

|  | % |
|---|---|
| (1) Vitamin A | 0.00001 |
| (2) Microcrystalline wax | 3.0 |
| (3) Beeswax | 3.0 |
| (4) Ceresin wax | 5.0 |
| (5) Liquid paraffin | 19.0 |
| (6) Squalane | 20.0 |
| (7) Carnauba wax | 3.0 |
| (8) Candellira wax | 3.0 |
| (9) Glycyrrhizinic stearyl | 5.0 |
| (10) Mixed colorant | 7.0 |
| (11) Dibutyl hydroxytoluene | 0.05 |
| (12) Perfume | q.s. |
| (13) Lanolin | Balance |

(Preparation Method)

The lipstick was obtained in a conventional way. The present lipstick prevented the formation of roughening on the lip.

Example 3-10: Emulsion

|  | % |
|---|---|
| (1) Vitamin A | 1.0 |
| (2) Hydrocortisone acetate | 0.05 |
| (3) Ethanol | 2.0 |
| (4) Glycerol | 10.0 |
| (5) Mannitol | 3.0 |
| (6) Propylene glycol | 3.0 |
| (7) Carboxyvinyl polymer | 0.3 |
| (8) KOH | 0.1 |
| (9) Methyl paraben | 0.1 |
| (10) Cetanol | 2.5 |
| (11) Vaseline | 2.0 |
| (12) Squalane | 10.0 |
| (13) Isopropyl myristate | 5.0 |
| (14) Glyceryl monostearate | 2.0 |
| (15) POE(25 mol) cetyl ether | 2.0 |
| (16) Purified water | Balance |

(Preparation Method)

The present emulsion was obtained in a conventional way. The present emulsion exhibited excellent skin improvement effects.

Example 3-11: Emulsion

|  | % |
|---|---|
| (1) Vitamin A | 0.3 |
| (2) Indomethacin | 0.3 |
| (3) Ethanol | 5.0 |
| (4) Glycerol | 5.0 |
| (5) Propylene glycol | 5.0 |
| (6) Carboxyvinyl polymer | 0.2 |
| (7) KOH | 0.06 |
| (8) Methyl paraben | 0.2 |
| (9) POE(60 mol) hydrogenated castor oil | 1.0 |
| (10) Squalane | 3.0 |
| (11) Isopropyl myristate | 3.0 |
| (12) Purified water | Balance |

(Preparation Method)

The present emulsion was obtained in a conventional way. The present emulsion exhibited excellent skin improvement effects.

Example 3-12: Night Cream

|  | % |
|---|---|
| (1) Squalane | 10.0 |
| (2) Liquid paraffin | 10.0 |
| (3) Vaseline | 3.0 |
| (4) Cetyl octanoate | 10.0 |
| (5) Dibutyl phthalate | 5.0 |
| (6) Glycyrrhizinic stearyl | 0.1 |
| (7) Indomethacin | 0.2 |
| (8) Butyl paraben | 0.2 |
| (9) Diglycerine triisostearate | 2.0 |
| (10) Diglycerine monoisostearate | 1.5 |
| (11) Vitamin A | 0.1 |
| (12) Glycerol | 10.0 |
| (13) Propylene glycol | 6.0 |
| (14) Purified water | Balance |

(Preparation Method)

The present night cream was obtained in a conventional way. The present night cream exhibited excellent skin improvement effects.

[Industrial Applicability]

The external skin treatment composition according to the present invention are useful as an external skin treatment composition capable of preventing the epidermal disabilities and synergistically of improving the changes and disabilities due to aged skins or sunlight exposure, with taking safety into consideration.

We claim:

1. An external skin treatment composition comprising (i) 0.00001 to 5.0% by weight of vitamin A and (ii) at least one skin roughening improvement aid selected from the group consisting of (a) 0.1 to 20% by weight of polyoxyalkylene modified organopolysiloxanes having a molecular weight of at least 3000, and selected from the group consisting of the compounds represented by the formulae (A), (B), (C) and (D), wherein R represents an alkyl group having 1 to 3 carbon atoms or a phenyl group, R' is hydrogen or an alkyl group having 1 to 12 carbon atoms, p is an integer of 1 to 5, m is an integer of 5 to 100, n and x are an integer of 1 to 50, and t and y are an integer of 0 to 50:

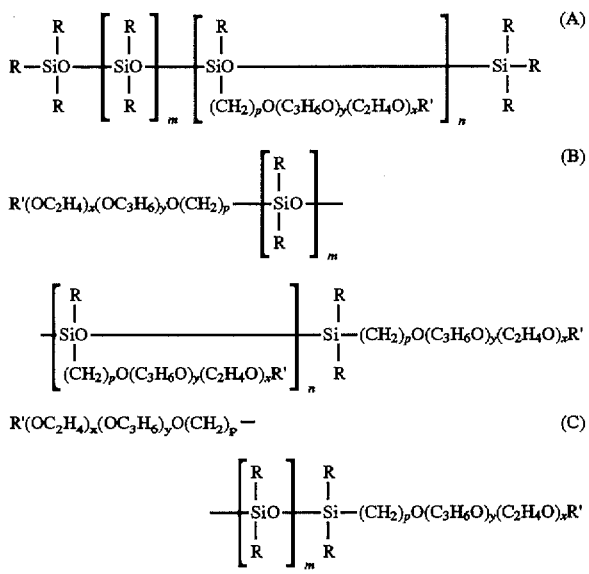

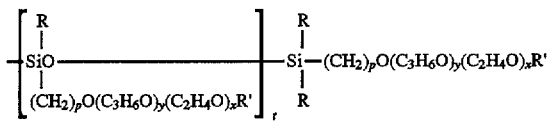

(b) at least 0.1% by weight of at least one compound selected from the group consisting of gentianose, umbelliferose, planteose, α,α-trehalose, raffinose, umbilicin, stachyose, verbascoses, maltiol, maltriose, erythritol and xylitose.

2. An external skin treatment composition as claimed in claim 1, wherein the at least one skin roughening improvement aid includes the polyoxyalkylene modified organopolysiloxane and further comprises one or more of lactose, sorbitol and mannitol.

3. A composition according to claim 1, wherein the amount of the vitamin A formulated in the composition is 0.0001 to 0.5% by weight and the amount of the polyoxyalkylene modified organopolysiloxane formulated in the composition is 0.2 to 10% by weight.

4. A composition according to claim 1, wherein the skin roughening improvement aid includes the at least one compound (b), and the amount of vitamin A formulated in the composition is 0.0001 to 0.5% by weight and the amount of the at least one compound (b) formulated in the composition is 0.5 to 50% by weight.

* * * * *